(12) United States Patent
Allen et al.

(10) Patent No.: US 6,534,486 B1
(45) Date of Patent: Mar. 18, 2003

(54) 2-(PURIN-9-YL)-TETRAHYDROFURAN-3,4-DIOL DERIVATIVES

(75) Inventors: David George Allen, Stevenage (GB); Chuen Chan, Stevenage (GB); Caroline Mary Cook, Stevenage (GB); Richard Peter Charles Cousins, Stevenage (GB); Brian Cox, Stevenage (GB); Hazel Joan Dyke, Cambridge (GB); Frank Ellis, Stevenage (GB); Joanna Victoria Geden, Aston Science Park (GB); Heather Hobbs, Stevenage (GB); Suzanne Elaine Keeling, Stevenage (GB); Alison Judith Redgrave, Stevenage (GB); Stephen Swanson, Stevenage (GB); Caroline Whitworth, Stevenage (GB); David Bays, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/720,193

(22) PCT Filed: Jun. 23, 1999

(86) PCT No.: PCT/EP99/04270

§ 371 (c)(1),
(2), (4) Date: Feb. 23, 2001

(87) PCT Pub. No.: WO99/67266

PCT Pub. Date: Dec. 29, 1999

(30) Foreign Application Priority Data

Jun. 23, 1998 (GB) .............................. 9813535

(51) Int. Cl.$^7$ .......................... A01N 43/04; A61K 31/70
(52) U.S. Cl. ........................... 514/46; 514/45; 514/826; 514/851; 514/921; 514/925; 536/27.13; 536/27.21; 536/27.81; 544/264; 544/251
(58) Field of Search .............................. 514/45, 46, 47, 514/826, 851, 885, 921, 925; 536/27.13, 27.21, 27.81; 544/264, 251

(56) References Cited

FOREIGN PATENT DOCUMENTS

| DE | 26 21 470 A | 12/1977 |
|----|----|----|
| WO | WO 94 17090 A | 8/1994 |
| WO | WO 96 02553 A | 2/1996 |
| WO | WO 98 01459 A | 1/1998 |

OTHER PUBLICATIONS

A. Rosowsky et al.: "Synthesis of the 2–Chloro Analogs of 3'–deoxyadenosine, 2',3'–Deoxyadenosine, and 2',3'–didehydro-2',3'–deoxyadenosine as Potential Antiviral Agents." Journal of Medicinal Chemistry., vol. 32, No. 5, May 1989, pp. 1135–1140.

K. Isono et al.: "Ascamycin and Dealanylascamycin, Nucleoside Antibiotics from Streptomyces sp.", Journal of Antibiotics, vol. XXXVII, No. 6, Jun. 1984, pp. 670–672.

*Primary Examiner*—James O. Wilson
*Assistant Examiner*—Patrick T. Lewis

(57) ABSTRACT

A series of 2-(Purin-9-yl)-tetrahydrofuran-3,4-diol derivatives with broad anti-inflammatory properties which inhibit leukocyte recruitment and activation and which are agonists of the adenosine 2a receptor are described.

16 Claims, No Drawings

2-(PURIN-9-YL)-TETRAHYDROFURAN-3,4-DIOL DERIVATIVES

This application is filed pursuant to 35 U.S.C. §371 as a United States National Phase Application of International Application No. PCT/EP99/04270 filed Jun. 23, 1990, which claims priority from GB9813535.3 filed Jun. 23, 1998.

This invention relates to new chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine A2a receptor will have anti-inflammatory actions. The area has been reviewed by Cronstein (1994). Studies on isolated neutrophils show an A2 receptor-mediated inhibition of superoxide generation, degranulation, aggregation and adherence (Cronstein et al, 1983 and 1985; Burkey and Webster, 1993; Richter, 1992; Skubitz et al, 1988. When agents selective for the A2a receptor over the A2b receptor (eg CGS21680) have been used, the profile of inhibition appears consistent with an action on the A2a receptor subtype (Dianzani et al, 1994). Adenosine agonists may also down-regulate other classes of leucocytes (Elliot and Leonard, 1989; Peachell et al, 1989). Studies on whole animals have shown the anti-inflammatory effects of methotrexate to be mediated through adenosine and A2 receptor activation (Asako et al, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschorn, 1993).

Certain substituted 4'-carboxamido and 4'-thioamido adenosine derivatives which are useful for the treatment of inflammatory diseases are described in International Patent Application Nos. WO94/17090, WO96/02553, WO96/02543 (Glaxo Group). Substituted 4'-carboxamidoadenosine derivatives useful in the treatment of dementia are described in AU 8771946 (Hoechst Japan). Substituted 4'-hydroxymethyl adenosine derivatives which are useful for the treatment of gastrointestinal motility disorders are described in EP-A-423776 and EP-A-423777 (Searle). Substituted 4'-hydroxymethyl adenosine derivatives which are useful as platelet aggregation inhibitors are described in BE-768925 (Takeda). 4'-Hydroxymethyl adenosine derivatives and 4'-esters thereof which are useful as antihypertensive agents or have other cardiovascular activity are described in U.S. Pat. No. 4,663,313, EP 139358 and U.S. Pat. No. 4,767,747 (Warner Lambert), U.S. Pat. No. 4,985,409 (Nippon Zoki) and U.S. Pat. No. 5,043,325 (Whitby Research). 4-Hydroxymethyladenosine derivatives useful in the treatment of autoimmune disorders are described in U.S. Pat. No. 5,106,837 (Scripps Research Institute). 4'-Hydroxymethyladenosine derivatives useful as anti-allergic agents are described in U.S. Pat. No. 4,704,381 (Boehringer Mannheim). Certain 4'-tetrazolylalkyl adenosine derivatives which are useful in the treatment of heart and circulatory disorders are generically described in DT-A-2621470 (Pharma-Waldhof. Other 4'-carboxamidoadenosine derivatives useful in the treatment of cardiovascular conditions are described in U.S. Pat. No. 5,219,840, GB 2203149 and GB 2199036 (Sandoz), WO94/02497 (US Dept. Health), U.S. Pat. No. 4,968,697 and EP 277917 (Ciba Geigy), U.S. Pat. No. 5,424,297 (Univ. Virginia) and EP 232813 (Warner Lambert). Other 4'-carboxamidoadenosine derivatives lacking substitution on the purine ring in the 2-position are described in DT 2317770, DT 2213180, U.S. Pat. Nos. 4,167,565, 3,864,483 and 3,966,917 (Abbott Labs), DT 2034785 (Boehringer Mannheim), JP 58174322 and JP 58167599 (Tanabe Seiyaku), WO92/05177 and U.S. Pat. No. 5,364,862 (Rhone Poulenc Rorer), EP 66918 (Procter and Gamble), WO86/00310 (Nelson), EP 222330, U.S. Pat. No. 4,962,194, WO88/03147 and WO88/03148 (Warner Lambert) and U.S. Pat. No. 5,219,839, WO95/18817 and WO93/14102 (Lab UPSA). 4'-Hydroxymethyladenosine derivatives lacking substitution on the purine ring in the 2-position are described in WO95/11904 (Univ Florida). 4'-Substituted adenosine derivatives useful as adenosine kinase inhibitors are described in WO94/18215 (Gensia). Other 4'-halomethyl, methyl, thioalkylmethyl or alkoxymethyl adenosine derivatives are described in EP 161128 and EP 181129 (Warner Lambert) and U.S. Pat. No. 3,983,104 (Schering). Other 4'-carboxamidoadenosine derivatives are described in U.S. Pat. No. 7,577,528 (NIH), WO91/13082 (Whitby Research) and WO95/02604 (US Dept Health).

Certain tetrazole containing deoxynucleotides which were found to lack anti-infective activity are described in Baker et al (1974) Tetrahedron 30, 2939–2942. Other tetrazole containing adenosine derivatives which show activity as platelet aggregation inhibitors are described in Mester and Mester (1972) Pathologie-Biologie, 20 (Suppl) 11–14. Certain nitrile containing ribose derivatives are described in Schmidt et al (1974) Liebigs. Ann. Chem. 1856–1863.

Other publications include: WO 98/16539 (Novo Nordisk A/S) which describes adenosine derivatives for the treatment of myocardial and cerebral ischaemia and epilepsy; WO 98/01426 (Rhone-Poulenc Rorer Pharmaceuticals Inc.) which relates to adenosine derivatives possessing antihypertensive, cardioprotective, anti-ischaemic and anti-lipolytic properties; and WO 98/01459 (Novo Nordisk A/S) which describes N,9-disubstituted adenine derivatives which are substituted in the 4'position by unsubstituted oxazolyl or isoxazolyl and the use of such compounds for the treatment of disorders involving cytokines in humans. WO 98/28319 (Glaxo Group Limited) was published subsequent to the earliest priority date of this application and describes 4'-substituted tetrazole 2-(purin-9-yl)-tetrahydrofuran-3,4-diol derivatives;

We have now found a novel group of compounds with broad anti-inflammatory properties which inhibit leukocyte recruitment and activation and which are agonists of the adenosine 2a receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses are severely limited by their side-effect profiles.

More particularly, the compounds of this invention may show an improved profile over known A2a-selective agonists in that they generally lack agonist activity at the human A3 receptor. This profile can be considered of benefit as A3 receptors are also found on leucocytes (eg eosinophil) and other inflammatory cells (eg mast cell) and activation of these receptors may have pro-inflammatory effects (Kohno et al, 1996; Van Schaick et al 1996). It is even considered that the bronchoconstrictor effects of adenosine in asthmatics may be mediated via the adenosine A3 receptor (Kohno et al, 1996).

Thus, according to the invention we provide compounds of formula (I):

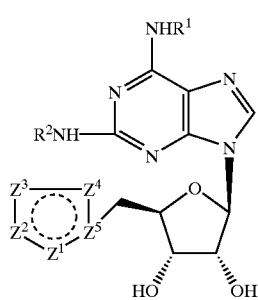

(I)

wherein $R_1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5$N—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more (e.g. 1, 2 or 3) —(CH$_2$)$_p$R$^6$ groups;
(xii) H$_2$NC(=NH)NHC$_{1-6}$alkyl-;
(xiii) a group of formula

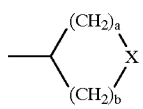

or such a group in which one methylene carbon atom adjacent to X, or both if such exist, is substituted by methyl;
(xiv) —$C_{1-6}$alkyl-OH;
(xv) —$C_{1-8}$haloalkyl;

(xvi) a group of formula

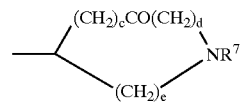

(xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$ where f is 2 or 3 and g is an integer 0 to 2;

$Z^5$ represents N;

$Z^1$, $Z^2$, $Z^3$ and $Z^4$ together with $Z^5$ form a 5-membered heterocyclic aromatic ring;

$R^4$ and $R^5$ independently represent hydrogen, $C_{1-6}$alkyl, aryl, aryl$C_{1-6}$alkyl- or NR$^4$R$^5$ together may represent pyridinyl, pyrrolidinyl, piperidinyl, morpholinyl, azetidinyl, azepinyl, piperazinyl or N—$C_{1-6}$ alkylpiperazinyl;

$R^6$ represents OH, NH$_2$, NHCOCH$_3$ or halogen;

$R^7$ represents hydrogen, $C_{1-6}$alkyl, —$C_{1-6}$alkylaryl or —COC$_{1-6}$alkyl;

X represents NR$^7$, O, S, SO or SO$_2$;

p represents 0 or 1;

a and b independently represent an integer 0 to 4 provided that a+b is in the range 3 to 5;

c, d and e independently represent an integer 0 to 3 provided that c+d+e is in the range 2 to 3;

and salts and solvates thereof.

$Z^1$, $Z^2$, $Z^3$ and $Z^4$ will independently represent C, N, O or S and, in the case of C and N, together with a sufficient number of hydrogen atoms to provide the ring with aromatic character. At least one of $Z^1$, $Z^2$, $Z^3$, and $Z^4$ will represent carbon. We prefer that one or two of $Z^1$, $Z^2$, $Z^3$, and $Z^4$ represent N and the remainder represent C. Carbon atoms in the ring may be substituted by hydroxy.

References to $C_{x-y}$alkyl include references to an aliphatic hydrocarbon grouping containing x to y carbon atoms which may be straight chain or branched and may be saturated or unsaturated. References to alkoxy may also be interpreted similarly.

References to aryl include references to mono- and bicyclic carbocyclic aromatic rings (e.g. phenyl, naphthyl) and heterocyclic aromatic rings, for example containing 1–3 hetero atoms selected from N, O and S (e.g. pyridinyl, pyrimidinyl, thiophenyl, imidazolyl, quinolinyl, furanyl, pyrrolyl, oxazolyl) all of which may be optionally substituted, e.g. by $C_{1-6}$alkyl, halogen, hydroxy, nitro, $C_{1-6}$alkoxy, cyano, amino, SO$_2$NH$_2$ or —CH$_2$OH.

Examples of $C_{3-8}$cycloalkyl for R$^1$ and R$^2$ include monocyclic alkyl groups (e.g. cyclopentyl, cyclohexyl) and bicyclic alkyl groups (e.g. norbornyl such as exo-norborn-2-yl).

Examples of (aryl)$_2$CHCH$_2$— for R$^1$ and R$^2$ include Ph$_2$CHCH$_2$— or such a group in which one or both phenyl moieties is substituted, e.g. by halogen or $C_{1-4}$alkyl.

Examples of $C_{3-8}$cycloalkyl$C_{1-6}$alkyl- for R$_1$ and R$^2$ include ethylcyclohexyl.

Examples of $C_{1-8}$alkyl for R$^1$ and R$^2$ include —(CH$_2$)$_2$C(Me)$_3$, —CH(Et)$_2$ and CH$_2$=C(Me)CH$_2$CH$_2$—.

Examples of arylC$_{1-6}$alkyl- for R$^1$ and R$^2$ include —(CH$_2$)$_2$Ph, —CH$_2$Ph or either in which Ph is substituted (one or more times) by halogen (e.g. iodine), amino, methoxy, hydroxy, —CH$_2$OH or SO$_2$NH$_2$; —(CH$_2$)$_2$ pyridinyl (e.g. —(CH$_2$)$_2$pyridin-2-yl) optionally substituted by amino; (CH$_2$)$_2$imidazolyl (e.g. 1H-imidazol-4-yl) or this group in which imidazoyl is N-substituted by C$_{1-6}$alkyl (especially methyl).

Examples of R$^4$R$^5$N—C$_{1-6}$alkyl- for R$^1$ and R$^2$ include ethyl-piperidin-1-yl, ethyl-pyrrolidin-1-yl, ethyl-morpholin-1-yl, —(CH$_2$)$_2$NH(pyridin-2-yl) and —(CH$_2$)$_2$NH$_2$.

Examples of C$_{1-6}$alkyl-CH(CH$_2$OH)— for R$^1$ and R$^2$ include Me$_2$CHCH(CH$_2$OH)—.

Examples of arylC$_{1-5}$alkyl-CH(CH$_2$OH)— for R$^1$ and R$^2$ include PhCH$_2$CH(CH$_2$OH)— particularly

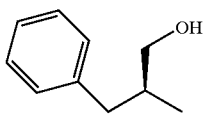

Examples of arylC$_{1-5}$alkyl-C(CH$_2$OH)$_2$— for R$^1$ and R$^2$ include PhCH$_2$C(CH$_2$OH)$_2$—.

Examples of C$_{3-8}$ cycloalkyl independently substituted by one or more —(CH$_2$)$_p$R$^6$ groups (eg 1, 2 or 3 such groups) for R$^1$ and R$^2$ include 2-hydroxy-cyclopentyl and 4-aminocyclohexyl (especially trans-4-amino-cyclohexyl).

Examples of H$_2$NC(=NH)NHC$_{1-6}$alkyl for R$^1$ and R$^2$ include H$_2$NC(=NH)NH(CH$_2$)$_2$—.

Examples of groups of formula

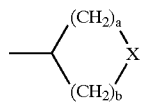

for R$^1$ and R$^2$ include pyrrolidin-3-yl, piperidin-3-yl, piperidin-4-yl, tetrahydro-1,1-dioxide thiophen-3-yl, tetrahydropyran-4-yl, tetrahydrothiopyran-4-yl and 1,1-dioxo-hexahydro-1.lamda.6-thiopyran-4-yl, or a derivative in which the ring nitrogen is substituted by C$_{1-6}$alkyl (e.g. methyl), C$_{1-6}$alkylacyl (e.g. acetyl), arylC$_{1-6}$alkyl- (e.g. benzyl).

Examples of —C$_{1-6}$alkyl-OH groups for R$^1$ and R$^2$ include —CH$_2$CH$_2$OH and —CH(CH$_2$OH)CH(CH$_3$)$_2$.

Examples of C$_{1-8}$haloalkyl for R$^1$ and R$^2$ include —CH$_2$CH$_2$Cl and (CH$_3$)$_2$ClC(CH$_2$)$_3$—.

Examples of groups of formula

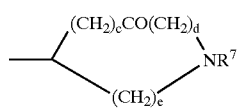

for R$^1$ and R$^2$ include 2-oxopyrrolidin-4-yl, 2-oxopyrrolidin-3-yl or a derivative in which the ring nitrogen is substituted by C$_{1-6}$alkyl (e.g. methyl) or benzyl.

Examples of aryl for R$^1$ and R$^2$ include phenyl optionally substituted by halogen (e.g. fluorine, especially 4-fluorine).

An example of a —(CH$_2$)$_f$SO$_2$NH$_g$(C$_{1-4}$alkyl)$_{2-g}$ group for R$^1$ and R$^2$ is —(CH$_2$)$_2$SO$_2$NHMe, and an example of a —(CH$_2$)$_f$SO$_2$NH$_g$(arylC$_{1-4}$alkyl)$_{2-g}$ group for R$^1$ and R$^2$ is —(CH$_2$)$_2$SO$_2$NHCH$_2$Ph.

An example of C$_{1-6}$alkyl for R$^7$ is methyl, an example of C$_{1-4}$alkylaryl for R$^7$ is benzyl, and an example of —COC$_{1-6}$alkyl for R$^7$ is acetyl.

We prefer that R$^1$ and R$^2$ do not both represent hydrogen.

We prefer R$^1$ to represent aryl$_2$CHCH$_2$—, C$_{1-6}$alkyl, hydrogen or arylC$_{1-6}$alkyl.

We prefer R$^2$ to represent trans-4-amino-cyclohexyl, 2-(1-methyl-1H-imidazoyl-4-yl)CH$_2$CH$_2$—, ethyl-morpholin-1-yl, pyrrolidin-3-yl, or 2-hydroxy-cyclopentyl.

We prefer R$^4$ and R$^5$ independently to represent hydrogen or aryl or NR$^4$R$^5$ together to represent pyrrolidinyl, piperidinyl, morpholinyl, azetidinyl, azepinyl, piperazinyl or N-methylpiperazinyl.

We prefer that p represents 0. We prefer that R$^6$ represents OH or NH$_2$.

We prefer that a represents 2 and that b represents 1 or 2. We prefer X to represent NR$^7$ (e.g. NH), O, S or SO$_2$, particularly O, S or NH.

We prefer that c represents 0, and either that d represents 1 and e represents 1 or d represents 0 and e represents 2. We prefer that R$^7$ represents hydrogen.

We particularly prefer R$^1$ to represent Ph$_2$CHCH$_2$—, hydrogen, PhCH$_2$CH$_2$—, or CH(Et)$_2$, especially Ph$_2$CHCH$_2$—.

We particularly prefer R$^2$ to represent 2-(1-methyl-1H-imidazoyl-4-yl)CH$_2$CH$_2$—.

We prefer that the moiety

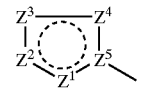

represents one of the following groups:

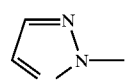
(I)

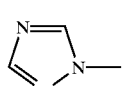
(II)

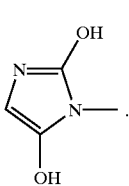
(III)

Highly preferred compounds herein have formula (Ia) in which R$^{2a}$, R$^{1a}$ and the ring comprising Z$^1$–Z$^5$ are as defined in the table below:

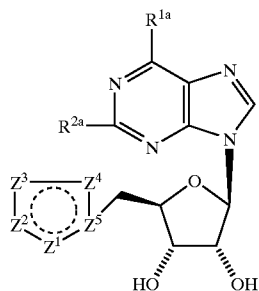
(Ia)
| R²ᵃ | R¹ᵃ | Ring comprising Z¹—Z⁵ |
|---|---|---|
| 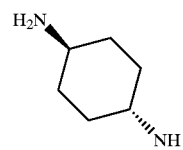 | 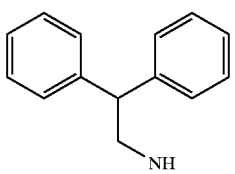 | 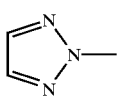 |
| 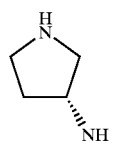 | 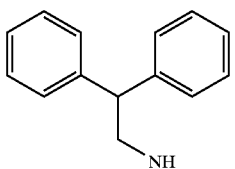 | 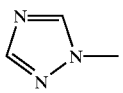 |
| 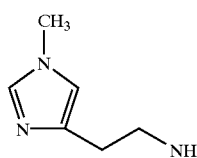 | 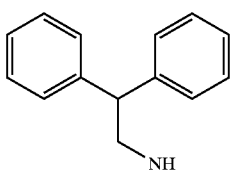 | 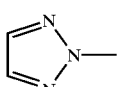 |
| 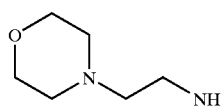 | | 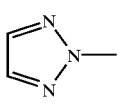 |
| 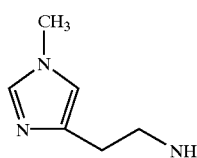 |  | 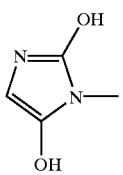 |
| 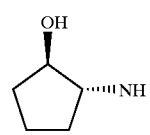 | 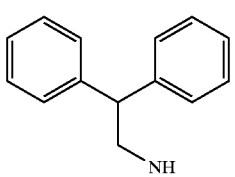 | 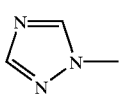 |

The representation of formula (I) indicates the absolute stereochemistry. When sidechains contain chiral centres the invention extends to mixtures of enantiomers (including racemic mixtures) and diastereoisomers as well as individual enantiomers. Generally it is preferred to use a compound of formula (I) in the form of a purified single enantiomer.

We also provide a first process for the preparation of compounds of formula (I) including the step of reacting a compound of formula (II)

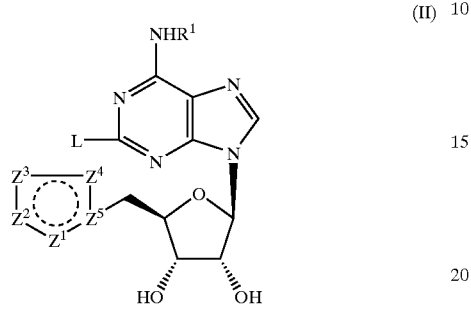

wherein L represents a leaving group, e.g. halogen, particularly chlorine; or a protected derivative thereof with a compound of formula $R^2NH_2$ or a protected derivative thereof. Said reaction will generally involve heating the reagents to a temperature of 50° C.–150° C. in the presence of an inert solvent such as DMSO. The compound of formula (II) may be used in a form which the two hydroxyl groups are protected e.g. with acetonide or acetyl groups. Compounds of formula $R^2NH_2$ are either known or may be prepared by conventional methods known per se.

Compounds of formula (II) may be prepared by reacting a compound of formula (III).

Compounds of formula (II) or a protected derivative thereof may be prepared by reacting a compound of formula (III)

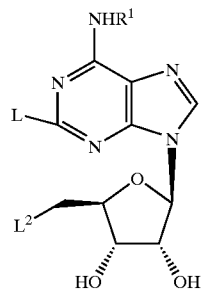

or a protected derivative thereof, where $L^2$ is a leaving group, with an appropriate heterocyclic ring (comprising $Z^1$, $Z^2$, $Z^3$, and $Z^4$). Where the parent heterocyclic ring is acidic, Mitsunobu conditions (e.g. $PPh_3$/DEAD in an inert solvent such as 1,4 dioxan) can be used. Where the parent heterocyclic ring is non-acidic, anion chemistry (e.g. NaH in an inert solvent, with $L^2$ comprising a suitably activated hydroxyl group such as trifluoromethylsulphonate) can be used. Compounds of formula (III) are either known or may be prepared by conventional methods including for example, methods analogous to those described at preparation 3. of PCT Patent Application No. WO94/17090.

Preferred reaction schemes herein comprise:

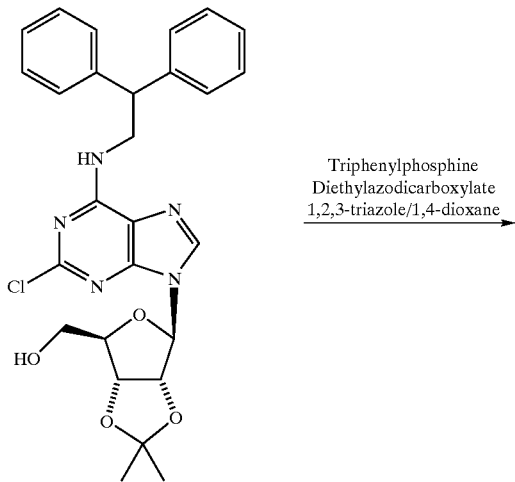

Prep 3 from WO94/17090

Triphenylphosphine
Diethylazodicarboxylate
1,2,4-triazole/1,4-dioxane

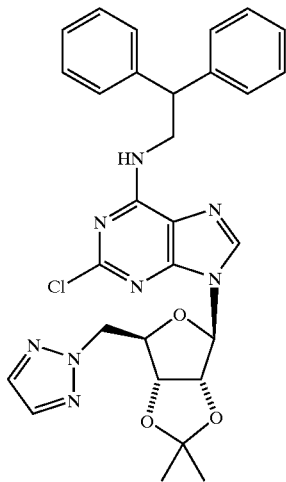

i) AcOH/H2O
ii) 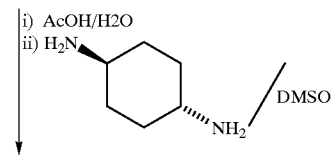 /DMSO

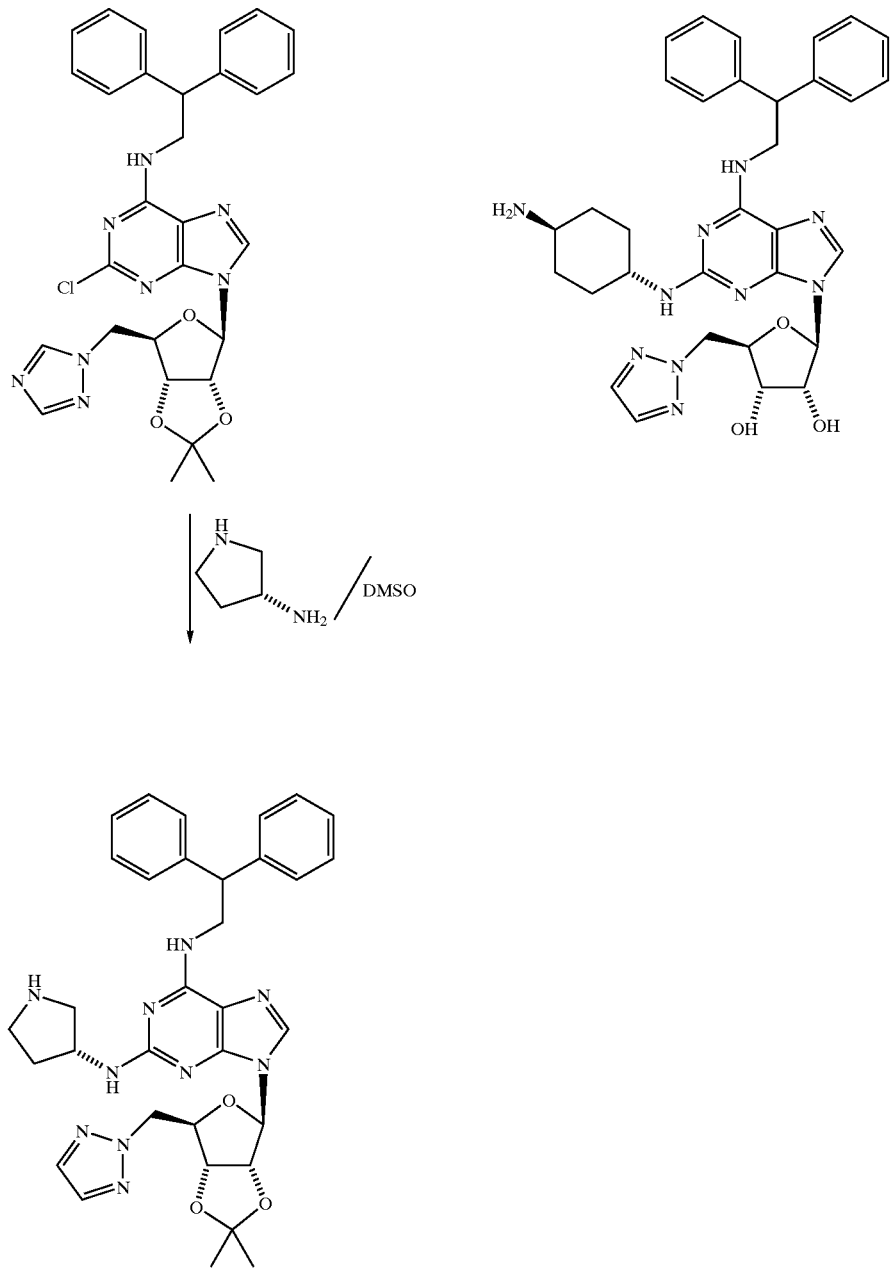

Another preferred reaction scheme herein comprises:

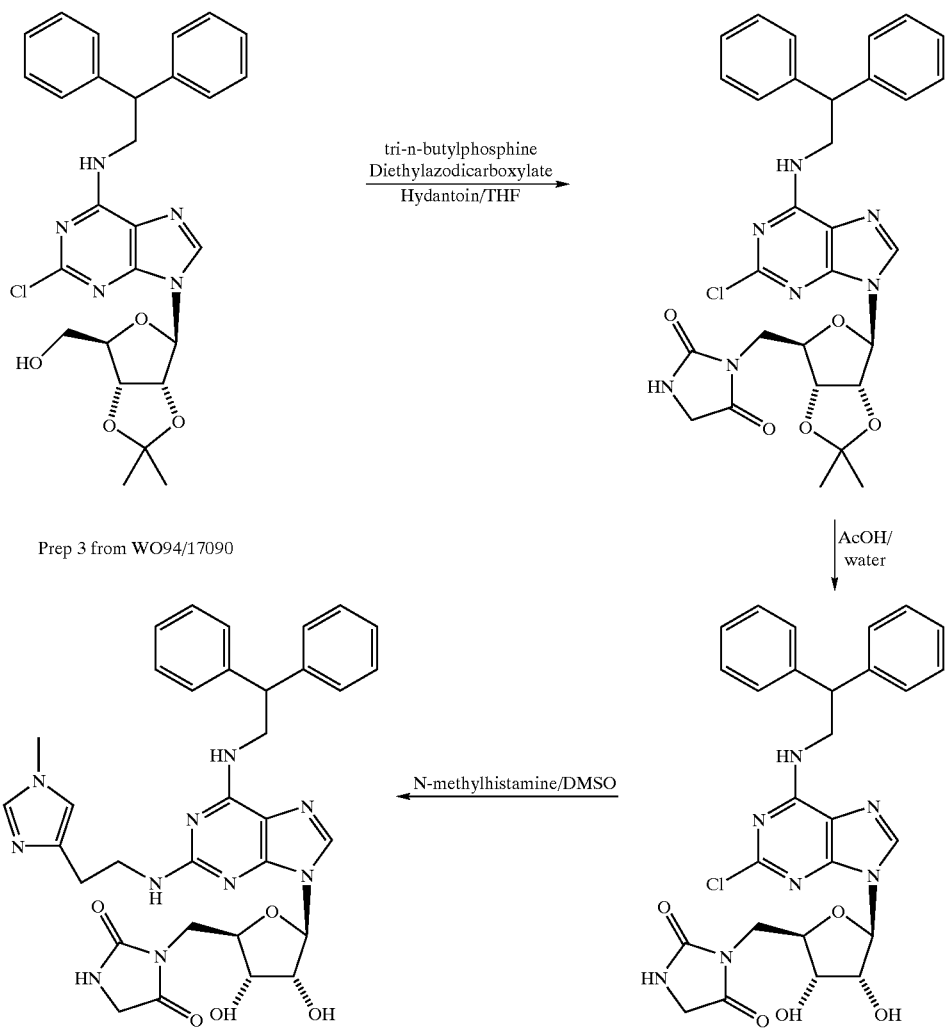

Prep 3 from WO94/17090

The R¹ and R² sidechains shown in the above schemes are merely illustrative and the skilled person will appreciate that the schemes are suitable for preparation of compounds of other R¹, R².

Examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl e.g. benzyloxycarbonyl or t-butoxycarbonyl) and arylalkyl (e.g. benzyl) which may be removed by hydrolysis or hydrogenolysis as appropriate. Suitable salts of the compounds of formula (I) include physiologically acceptable salts such as acid addition salts derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, methanesulphonates, and if appropriate, inorganic base salts such as alkali metal salts, for example sodium salts. Other salts of the compounds of formula (I) include salts which are not physiologically acceptable but may be useful in the preparation of compounds of formula (I) and physiologically acceptable salts thereof. Examples of such salts include trifluoroacetates and formates.

Examples of suitable solvates of the compounds of formula (I) include hydrates. Acid-addition salts of compounds of formula (I) may be obtained by treating a free-base of formula (I) with an appropriate acid.

The potential for compounds of formula (I) to inhibit leukocyte function may be demonstrated, for example, by their ability to inhibit superoxide ($O_2-$) generation from neutrophils stimulated with chemoattractants such as N-formylmethionyl-leucyl-phenylaianine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component e.g. Alzheimer's disease and multiple sclerosis. Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable carriers or excipients.

There is also provided a process for preparing such a pharmaceutical formulation which comprises mixing the ingredients.

The compounds according to the invention may, for example, be formulated for oral, buccal, parenteral, topical or rectal administration, preferably for parenteral or topical (e.g. by aerosol) administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluoroethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (eg sodium cromoglycate)) or beta adrenergic agents (such as salmeterol, salbutamol, formoterol, fenoterol or terbutaline and salts thereof) or antiinfective agents (eg antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

Certain intermediate compounds described herein are new and these are also provided as an aspect of the invention.

The compounds of the invention have the advantage that they may be more efficacious, show greater selectivity, have fewer side effects, have a longer duration of action, be more bioavailable by the preferred route, show less systemic activity when administered by inhalation or have other more desirable properties than similar known compounds. In particular the compounds of the invention have the advantage that they may show greater selectivity for the adenosine 2a receptor subtype over other adenosine receptor subtypes (especially the A1 and A3 receptor subtypes) than hitherto known compounds.

Compounds of the invention were tested for in vitro and in vivo biological activity in accordance with the following screens:

(1) Agonist activity against adenosine 2a, adenosine 1 and adenosine 3 receptor subtypes.

Agonist selectivity of compounds against other human adenosine receptors was determined using Chinese hamster ovary (CHO) cells transfected with the gene for the relevant human adenosine receptor following a method based on that of Castanon and Spevak, 1994. The CHO cells were also transfected with cyclic AMP response elements promoting the gene for secreted placental alkaline phosphatase (SPAP) (Wood, 1995). The effect of test compounds was determined by their effects on basal levels of cAMP (A2a) or on forskolin-enhanced cAMP (A1 and A3) as reflected by changes in levels of SPAP. $EC_{50}$ values for compounds were then determined as a ratio to that of the non-selective agonist N-ethyl carboxamide adenosine (NECA).

REFERENCES

Asako H, Wolf, R E, Granger, D N (1993), Gastroenterology 104, pp 31–37;
Bedford C D, Howd R A, Dailey O D, Miller A, Nolen H W III, Kenley R A, Kern J R,
Winterle J S, (1986), J. Med. Chem. 29, pp2174–2183;
Burkey T H, Webster, R O, (1993), Biochem. Biophys Acta 1175, pp 312–318;
Castanon M J, Spevak W, (1994), Biochem. Biophys Res. Commun. 198, pp 626–631;
Cronstein B N, Kramer S B, Weissmann G, Hirschhorn R, (1983), Trans. Assoc. Am. Physicians 96, pp 384–91;
Cronstein B N, Kramer S B, Rosenstein E D, Weissmann G, Hirschhorn R, (1985), Ann N.Y. Acad. Sci. 451, pp 291–301;1
Cronstein B N, Naime D, Ostad E, (1993), J. Clin. Invest. 92, pp 2675–82;
Cronstein B N, Naime D, Ostad E, (1994), Adv. Exp. Med. Biol., 370, pp 411–6;
Cronstein B N, (1994), J. Appl. Physiol. 76, pp 5–13;
Dianzani C, Brunelleschi S, Viano I, Fantozzi R, (1994), Eur. J. Pharmacol 263, pp 223–226;
Elliot K R F, Leonard E J, (1989), FEBS Letters 254, pp 94–98;
Flora K P, van't Riet B, Wampler G L, (1978), Cancer Research, 38, pp1291–1295;
Green P G, Basbaum A I, Helms C, Levine J D, (1991), Proc. Natl. Acad Sci. 88, pp 4162–4165;
Hirschorn R, (1993), Pediatr. Res 33, pp S35–41;
Kohno Y; Xiao-duo J; Mawhorter S D; Koshiba M; Jacobson K A. (1996).Blood 88 p3569–3574.
Peachell P T, Lichtenstein L M, Schleimer R P, (1989), Biochem Pharmacol 38, pp 1717–1725;
Richter J, (1992), J. Leukocyte Biol. 51, pp 270–275;
Rosengren S, Bong G W, Firestein G S, (1995), J. Immunol. 154, pp 5444–5451;
Sanjar S, McCabe P J, Fattah D, Humbles A A, Pole S M, (1992), Am. Rev. Respir. Dis. 145, A40;
Skubitz K M, Wickman N W, Hammerschmidt D E, (1988), Blood 72, pp 29–33
Van Schaick E A; Jacobson K A; Kim H O; Ijzerman A P; Danhof M. (1996) Eur J Pharmacol 308 p311–314.
Wood K V. (1995) Curr Opinion Biotechnology 6 p50–58.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention is illustrated by the following Examples:

EXAMPLES

General Experimental Details

Where products were purified by column chromatography, 'flash silica' refers to silica gel for chromatography, 0.040 to 0.063 mm mesh (e.g. Merck Art 9385), where column elution was accelerated by an applied pressure of nitrogen at up to 5 p.s.i. Where thin layer chromatography (TLC) has been used it refers to silica gel TLC using 5×10 cm silica gel 60 $F_{254}$ plates (e.g. Merck Art 5719).

Where products were purified by preparative HPLC, this was carried out on a C18-reverse-phase column (1" Dynamax), eluting with a gradient of acetonitrile (containing 0.1% trifluoroacetic acid) in water (containing 0.1% trifluoroacetic acid) and the compounds isolated as their trifluoroacetate salts unless otherwise specified.

Standard Automated Preparative HPLC Column, Conditions & Eluent

Automated preparative high performance liquid chromatography (autoprep. HPLC) was carried out using a Supelco ABZ+5 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 5–95% over 20 minutes.

LC/MS System

The Liquid Chromatography Mass Spectroscopy (LC/MS) systems used:

LC/MS System A—A Supelco ABZ+, 3.3 cm×4.6 mm i.d. column eluting with solvents: A—0.1% v/v formic acid+0.077% w/v ammonium acetate in water, and B—95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% B over 0.3 mins. Positive and negative electrospray ionization was employed.

LC/MS System B—A Supelco ABZ+, 5 cm×2.1 mm i.d. column eluting with solvents: A—0.1% v/v formic acid +0.077% w/v ammonium acetate in water, and B—95:5 acetonitrile:water +0.05% v/v formic acid. The following gradient protocol was used: 0–100% B over 3.5 mins: hold at 100% B for 1.50 mins; return to 0% B over 0.50 mins. Positive and negative electrospray ionization was employed.

Intermediate 1: [2-Chloro-9-(2,2-dimethyl-6R-[1,2,3] triazol-2-ylmethyl-tetrahydro-(3aR,6aR)-furo[3,4-d][1,3] dioxol-4R-yl)-9H-purin-6-yl]-(2,2-diphenyl-ethyl)-amine 6R-[2-Chloro-6-(2,2-diphenyl-ethyl)-amino-purin-9-yl]-2,2-dimethyl-tetrahydro-(3aR,6aR)-furo[3,4-d][1,3]dioxol-4R-yl]-methanol [Preparation 3 from WO94/17090] (0.1 g), triphenylphosphine (0.081 g), 1,2,3-triazole (0.021 g), in 1,4-dioxan (3 ml) were treated with diethylazodicarboxylate (0.05 ml) and stirred at room temperature for 16 hours. The solvent was removed in vacuo. Purification by column chromatography (twice) on flash silica eluting first with ethylacetate:cyclohexane 1:2, then with dichloromethane:ethanol:ammonia (200:8:1) yielded the title compound as colourless gum (0.078 g).

TLC $SiO_2$ (ethyl acetate:cyclohexane, 1:1) Rf=0.3

Intermediate 1: (Alternative method): [2-Chloro-9-(2,2-dimethyl-6R-[1,2,3]triazol-2-ylmethyl-tetrahydro-(3aR,6aR)-furo[3,4-d][1,3]dioxol-4R-yl)-9H-purin-6-yl]-(2,2diphenyl-ethyl)-amine 6R-[2-Chloro-6-(2,2-diphenyl-ethyl)-amino-purin-9-yl]-2,2-dimethyl-tetrahydro-(3aR,6aR)-furo[3,4-d][1,3]dioxol-4R-yl]-methanol [Preparation 3 from WO94/17090] (0.7 g), tri-n-butylphosphine (0.407 g), 1,2,3-triazole (0.116 ml), 1,1'-(Azodicarbonyl)dipiperidine (0.507 g) in THF (12 ml) were heated at 50° C. for 7 hours. The cooled mixture was treated with water (50 ml) , extracted with ethyl acetate (2×50 ml), dried (sodium sulphate) and evaporated in vacuo. The residue was treated with dichloromethane (10 ml), filtered. Purification of the filtrate by column chromatography on flash silica eluting with ethyl acetate:cyclohexane (1:2) yielded the title compound as white foam (0.468 g). TLC $SiO_2$ (ethyl acetate:hexane, 1:1) Rf=0.46.

Intermediate 2: [2-Chloro-9-(2,2-dimethyl-6R-[1,2,4] triazol-1-ylmethyl-tetrahydro-(3aR,6aR)-furo[3,4-d][1,3] dioxol-4R-yl)-9H-purin-6-yl]-(2,2-diphenyl-ethyl)-amine 6R-[2-Chloro-6-(2,2-diphenyl-ethyl)-amino-purin-9-yl]-2,2-dimethyl-tetrahydro-(3aR,6aR)-furo[3,4-d][1,3]dioxol-4R-yl]-methanol [Preparation 3 from WO94/17090] (0.15 g), triphenylphosphine (0.118 g), 1,2,4-triazole (0.031 g) in 1,4-dioxan (5 ml) were treated with diethylazodicarboxylate (0.075 ml) and stirred at room temperature for 88 hours. The mixture was the concentrated to about 2 ml in vacuo, triphenylphosphine (0.073 mg), 1,2,4-triazole (0.019 g) and diethylazodicarboxyiate (0.075 ml) were added and the mixture heated at 50° C. for 16 hours. The solvent was removed in vacuo. Purification by column chromatography (twice) on flash silica eluting first with ethyl acetate/cyclohexane (2:1) yielded the title compound as a cream coloured foam (0.107 g). TLC $SiO_2$ (ethyl acetate:hexane, 2:1) Rf=0.16.

Intermediate 3: (2R,3R,4S,5R)-2-[2-Chloro-6-(2,2diphenyl-ethylamino)-purin-9-yl]-5-[1,2,3]triazol-2-ylmethyl-tetrahydro-furan-3,4-diol Intermediate 1 (0.468 g), acetic acid (20 ml) and water (5 ml) were heated at 100° C. for 4 hours. The cooled mixture was evaporated in vacuo, treated with saturated sodium bicarbonate solution (50 ml) , extracted with ethyl acetate (2×50 ml), dried (sodium sulphate) and evaporated in vacuo to give the title compound as a white foam (0.45 g). TLC $SiO_2$ (ethyl acetate:hexane, 1:1) Rf=0.05.

Intermediate 4: 3-{6R-[2-Chloro-6-(2,2-diphenylethylamino)-purin-9-yl]-2,2-dimethyl-tetrahydro-(3aR,6aR)-furo[3,4-d][1,3]dioxol-4R-ylmethyl}-imidazolidine-2,4dione 6R-[2-Chloro-6-(2,2-diphenyl-ethyl)-amino-purin-9-yl]-2,2-dimethyl-tetrahydro-(3aR,6aR)-furo[3,4-d][1,3]dioxol-4R-yl]-methanol [Preparation 3 from WO94/17090] (1 g), tri-n-butylphosphine (0.952 ml), diethylazodicarboxylate (0.51 ml), hydantoin (0.382 g) in tetrahydrofuran (12 ml) was heated at 70° C. for 48 hours. The cooled reaction mixture was evaporated in vacuo. Purification by column chromatography on flash silica eluting first with ethyl acetate/cyclohexane (2:1–4:1)-ethyl acetate yielded the title compound as a pale yellow oil (1 g). TLC $SiO_2$ (Dichloromethane, ethanol, 880 ammonia, (100:8:1)) Rf=0.48.

Intermediate 5: 3-{5R-[2-Chloro-6-(2,2-diphenylethylamino)-purin-9-yl]-3S ,4R-dihydroxy-tetrahydrofuran-2R-ylmethyl}-imidazolidine-2,4-dione Intermediate 4 (1 g), acetic acid (20 ml) and water (5 ml) were heated at 100 ° C. for 4 hours. Solvent removed in vacuo, treated with saturated sodium bicarbonate solution (50 ml), extracted with ethyl acetate (2×50 ml), dried (sodium sulphate) and evaporated in vacuo to yield the title compound as colourless oil (1.06 g). TLC $SiO_2$ (dichloromethane, ethanol, 880 ammonia, (100:8:1)) Rf=0.17,

Example 1

(2R,3R,4S, 5R)-2-[2-(trans-4-Amino-cyclohexylamino)6-(2,2-diphenyl-ethylamino)-purin-9-yl]-5-[1,2,3]triazol-2-ylmethyl-tetrahydro-furan-3,4-diol formate Intermediate 1 (0.078 g), acetic acid (4 ml) and water (1 ml) were heated at 100° C. for 2 hours. The cooled mixture was evaporated in vacuo and treated with saturated sodium carbonate solution (10 ml) and extracted with ethyl acetate (3×20 ml), dried (sodium sulphate) and evaporated in vacuo to give a colourless gum. The gum was dissolved in ethanol (20 ml), treated with sodium hydroxide (1 g) and left to stir for 16 hours at room temperature. The solvent was removed in vacuo, the residue was treated with water (50 ml), extracted with ethyl acetate (3×50ml), dried (sodium sulphate) and evaporated in vacuo. The residue was treated with dimethylsulphoxide (2 ml), trans-1,4-diaminocyclohexane (0.056 g) and heated at 90° C. in a sealed vial (eg Reactivial™) for 48 hours. Trans-1,4-diaminocyclohexane (0.056 g) was added and the mixture heated at 120° C. for 32 hours. The crude material was purified by Solid Phase Extraction (SPE) cartridge (NH2 aminopropyl Bondelute, 2 mL cartridge) eluted with dichloromethane (12 ml), ether (12 ml), ethyl acetate (12 ml), 10% methanol/ethyl acetate (12 ml), and methanol (12 ml). The 10% methanol/ethyl acetate and methanol fractions were combined and evaporated to dryness. Purification of by preparative HPLC (10–60% acetonitrile over 20 mins) afforded the after freeze-drying the title compound as a buff coloured foam (0.008 g). LC-MS System B Rt=2.48 min, m/z 611 (MH$^+$).

Example 2

(2R,3R,4S,5R)-2-[6-(2,2-Diphenyl-ethylamino)-2-(pyrrolidin-3R-ylamino)-purin-9-yl]-5-[1,2,4]triazol-1-ylmethyl-tetrahydro-furan-3,4-diol diformate Intermediate 2 (0.107 g), acetic acid (4 ml) and water (1 ml) were heated at 100° C. for 2.5 hours. The cooled mixture was evaporated in vacuo, dissolved in acetic acid (4 ml) and water (1 ml) and heated at 100° C. for 2 hours. The cooled mixture was evaporated in vacuo, treated with saturated aqueous sodium bicarbonate solution (10 ml) and extracted with ethyl acetate (2×10 ml), dried (sodium sulphate) and evaporated in vacuo to afford a pale yellow oil (0.096 g). An aliquot of this material (0.019 g) of this material was treated with (3R)-(+)-3-aminopyrrolidine (0.03 ml) in dimethylsulphoxide (0.07 ml) at 110° C. for 16 hours. Purification by Autoprep HPLC furnished after freeze drying the title compound as pale yellow solid (0.0108 g). LC-MS System A Rt=3.78 min, m/z 583 (MH$^+$).

Example 3

(2R,3R,4S,5R)-2-{6-(2,2-Diphenyl-ethylamino)-2-[2-(1-methyl-1-H-imidazol-4-yl)-ethylamino]-purin-9-yl}-5-[1,2,3]triazol-2-ylmethyl-tetrahydro-furan-3,4-diol diformate Intermediate 3 (0.043 g), 1-methylhistamine (0.051 g), dimethylsulphoxide (0.5 ml) in a sealed vial (eg Reactivial™) were heated at 90° C. for 16 hours, then at 100° C. for 16 hours. 1-Methylhistamine (0.051 g) was added and the mixture heated at 120° C. for 16 hours. Purification by Autoprep HPLC afforded after freeze-drying the title compound as a white solid (0.006 g). LC-MS System A Rt=3.71 min, m/z 622 (MH$^+$).

Example 4

(2R,3R,4S,5R)-2-[6-(2,2-Diphenyl-ethylamino)-2-(2-morpholin-4-yl-ethylamino)-purin-9-yl]-5-[1,2,3]triazol-2-ylmethyl-tetrahydro-furan-3,4-diol formate Intermediate 3 (0.043 mg), 4-(2-aminoethyl)morpholine (0.053 mg), dimethyl sulphoxide (0.05 ml) ) in a sealed vial (eg Reactivial™) were heated at 90° C. for 16 hours. Purification by Autoprep HPLC afforded after freeze-drying the title compound as a pale yellow solid (0.019 g). LC-MS System A Rt=3.71 min, m/z 627 (MH$^+$).

Example 5

3-(5R-{6-(2,2-Diphenyl-ethylamino)-2-[2-(1-methyl-1-H-imidazol-4-yl)-ethylamino]-purin-9-yl}3S,4R-dihydroxy-tetrahydro-furan-2R-ylmethyl)-imidazolidine-2,4-dione diformate Intermediate 5 (0.066 g), 1-methylhistamine (0.05 g) dimethylsulphoxide (0.05 ml) in a sealed vial (eg Reactivial™) were heated at 90° C. for 16 hours, and then at 110° C. for 16 hours. Purification byAutoprep HPLC afforded after freeze-drying the title compound as a cream coloured solid (0.008 g). LC-MS System A Rt=3.619 min, m/z 653 (MH$^+$).

Example 6

(2R,3R,4S,5R)-2-[6-(2,2-Diphenyl-ethylamino)-2-(2R-hydroxy-cyclopent-(R)-ylamino)-purin-9-yl]-5-[1,2,4]triazol-1-ylmethyl-tetrahydro-furan-3,4-diol format Intermediate 2 (0.414 g), acetic acid (20 ml) and water (5 ml) were heated at 100° C. for 3 hours. The cooled mixture was evaporated in vacuo, treated with aqueous saturated sodium bicarbonate solution (50 ml), extracted with ethyl acetate (2×50 ml), dried (sodium sulphate) and evaporated in vacuo to give a white foam (0.4 g). An aliquot of this material (0.038 g) of this material was treated with (R,R)-aminocyclopentan-2-ol (0.035 g), dimethylsulphoxide (0.05 ml) and heated in a sealed vial (eg Reactivial™) were heated at 90 ° C. for 16 h. Purification by Autoprep HPLC afforded after freeze-drying the title compound as a cream coloured solid (0.012 g). LC-MS System A Rt=4.02 min, m/z 598 (MH$^+$).

The compounds of the Examples were tested in screen (1) (agonist activity against receptor sub-types) and the results obtained were as follows:

| Example No. | A2a | A3 | A1 |
| --- | --- | --- | --- |
| 1 | 17.1 | >656 | >=3969 |
| 2 | 14.4 | >152 | >8479 |
| 3 | 1.31 | >147 | 3038.8 |
| 4 | 16.9 | >174 | 1014 |
| 5 | 13.46 | >270 | 8479 |
| 6 | 23.7 | >274 | >=3397 |

Values given in the Table are $EC_{50}$ values as a ratio of that of NECA.

| ABBREVIATIONS | |
|---|---|
| TMS | trimethylsilyl |
| TFA | trifluoroacetic acid |
| DMF | N,N-dimethylformamide |
| NECA | N-ethylcarboxamideadenosine |
| DMAP | 4-dimethylaminopyridine |
| TEMPO | 2,2,6,6-tetramethyl-1-piperidinyloxy, free radical |
| TMSOTf | Trimethylsilyltrifluoromethylsulphonate |
| DBU | 1,8-diazabicyclo[5.4.0]undec-7-ene |
| BSA | bistrimethylsilylacetamide |
| DCM | dichloromethane |
| DAST | diethylaminosulphur trifluoride |
| Ph | phenyl |
| CDI | carbonyldiimidazole |
| EEDQ | 2-ethoxy-1-ethoxycarbonyl-1,2 dihydroquinone |
| NSAID | non-steroidal antiinflammatory drug |
| DEAD | diethylazocarboxylate |

What is claimed is:

1. A compound of formula (I):

(I)

wherein $R^1$ and $R^2$ independently represent a group selected from:
(i) $C_{3-8}$cycloalkyl-;
(ii) hydrogen;
(iii) aryl$_2$CHCH$_2$—;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5$N—$C_{1-6}$alkyl-;
(viii) $C_{1-6}$alkyl-CH(CH$_2$OH)—;
(ix) aryl$C_{1-5}$alkyl-CH(CH$_2$OH)—;
(x) aryl$C_{1-5}$alkyl-C(CH$_2$OH)$_2$—;
(xi) $C_{3-8}$cycloalkyl independently substituted by one or more —(CH$_2$)$_p$R$^6$ groups;
(xii) H$_2$NC(=NH)NHC$_{1-6}$alkyl-;
(xiii) a group of formula or such a group in which one methylene carbon atom adjacent to X, or both if such exist, is substituted by methyl;
(xiv) —$C_{1-6}$alkyl-OH;
(xv) —$C_{1-8}$haloalkyl;

(xvi) a group of formula (xvii) aryl; and
(xviii) —(CH$_2$)$_f$SO$_2$NH$_g$(C$_{1-4}$alkyl-)$_{2-g}$ or —(CH$_2$)$_f$SO$_2$NH$_g$(arylC$_{1-4}$alkyl-)$_{2-g}$ where f is 2 or 3 and g is an integer 0 to 2; $Z^5$ represents N;

$Z^1$, $Z^2$, $Z^3$ and $Z^4$ together with the carbon atom form a 5-membered heterocyclic aromatic ring;

$R^4$ and $R^5$ independently represent hydrogen, $C_{1-6}$alkyl, aryl, aryl$C_{1-6}$alkyl- or NR$^4$R$^5$ together may represent pyridinyl, pyrrolidinyl, piperidinyl, morpholinyl, azetidinyl, azepinyl, piperazinyl or N—$C_{1-6}$alkylpiperazinyl;

$R^6$ represents OH, NH$_2$, NHCOCH$_3$ or halogen;

$R^7$ represents hydrogen, $C_{1-6}$alkyl, —$C_{1-6}$alkylaryl or —COC$_{1-6}$alkyl;

X represents NR$^7$, O, S, SO or SO$_2$;

p represents 0 or 1;

a and b independently represent an integer 0 to 4 provided that a+b is in the range 3 to 5;

c, d and e independently represent an integer 0 to 3 provided that c+d+e is in the range 2 to 3;

and salts and solvates thereof.

2. A compound according to claim 1 wherein $R^1$ and $R^2$ do not both represent hydrogen.

3. A compound according to claim 1 wherein $R^1$ represents aryl$_2$CHCH$_2$.C$_{1-6}$alkyl, hydrogen or arylC$_{1-6}$alkyl.

4. A compound according to claim 1 wherein $R^1$ represents Ph$_2$CHCH$_2$—.

5. A compound according to claim 1 wherein $R^2$ represents trans-4-amino-cyclohexyl, 2-(1-methyl-1H-imidazoyl-4-yl)CH$_2$CH$_2$—, ethyl-morpholin-1-yl, pyrrolidin-3-yl, or 2-hydroxy-cyclopentyl.

6. A compound according to claim 1 wherein $R^2$ represents 2-(1-methyl-1H-imidazoyl-4-yl)CH$_2$CH$_2$—.

7. A compound according to claim 1 wherein $R^4$ and $R^5$ independently represent hydrogen or aryl or NR$^4$R$^5$ together may represent pyrrolidinyl, piperidinyl, morpholinyl, azetidinyl, azepinyl, piperazinyl or N-methylpiperazinyl.

8. A compound according to claim 1 wherein $R^6$ represents OH or NH$_2$.

9. A compound according to claim 1 wherein X represents NR$^7$, O, S or SO$_2$.

10. A compound according to claim 1 wherein the moiety represents one of the following groups:

(I)

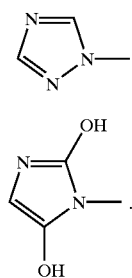

(III)

11. A compound of formula (I) according to claim 1 which is
(2R,3R,4S,5R)-2-[2-(trans-4-Amino-cyclohexylamino)-6(2,2-diphenyl-ethylamino)-purin-9-yl]-5-[1,2,3]triazol-2-ylmethyl-tetrahydro-furan-3,4-diol;
(2R,3R,4S,5R)-2-[6-(2,2-Diphenyl-ethylamino)-2-(pyrrolidin-3R-ylamino)-purin-9-yl]-5[1,2,4]triazol-1-ylmethyl-tetrahydro-furan-3,4-diol;
(2R,3R,4S,5R)-2-{6-(2,2-Diphenyl-ethylamino)-2-[2-(1-methyl-1H-imidazol-4-yl)-ethylamino]-purin-9-yl}-5-[1,2,3]triazol-2-ylmethyl-tetrahydro-furan-3,4-diol;
(2R,3R,4S,5R)-2-[6-(2,2-Diphenyl-ethylamino)-2-(2-morpholin-4-yl-ethylamino)-purin-9-yl]-5-[1,2,3]triazol-2-ylmethyl-tetrahydro-furan-3,4-diol;
3-(5R-{6-(2,2-Diphenyl-ethylamino)-2-[2-(1-methyl-1H-imidazol-4-yl)-ethylamino]-purin-9-yl}-3S,4R-dihydroxy-tetrahydro-furan-2R-ylmethyl)-imidazolidine-2,4-dione;
(2R,3R,4S,5R)-2-[6-(2,2-Diphenyl-ethylamino)-2-(2R-hydroxy-cyclopent-(R)-ylamino)-purin-9-yl]-5-[1,2,4]triazol-1-ylmethyl-tetrahydro-furan-3,4-diol;
or a salt or solvate of any one thereof.

12. A pharmaceutical composition comprising a compound of formula (I) as defined in claim 1 or a pharmaceutically acceptable salt or solvate thereof in admixture with one or more pharmaceutically acceptable diluents or carriers.

13. A compound of formula (I) as defined in claim 1 or a pharmaceutically acceptable salt or solvate thereof for use as a pharmaceutical.

14. A method of treating inflammatory diseases comprising administering to a patient an effective amount of a compound of formula (I) as defined in claim 1 or a pharmaceutically acceptable salt or solvate thereof.

15. A process for preparation of compounds of formula (I) as defined in claim 1 which comprises reacting a compound of formula (II)

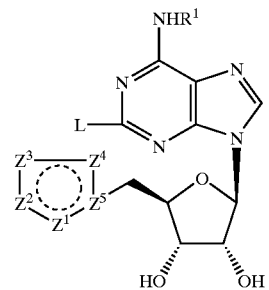

(II)

wherein L represents a leaving group or a protected derivative thereof with a compound of formula $R^2NH_2$ or a protected derivative thereof, wherein $R^1$, $Z^1$, $Z^2$, $Z^3$, $Z^4$ and $Z^5$ are as defined in claim 1.

16. A compound of formula (II)

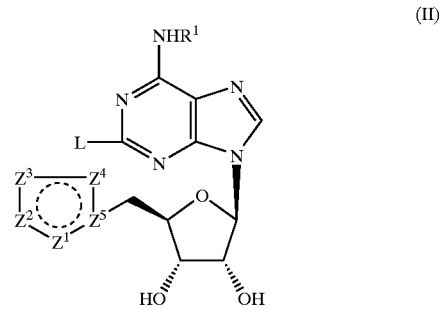

(II)

wherein L represents a leaving group or a protected derivative thereof and $R^1$, $Z^1$, $Z^2$, $Z^3$, $Z^4$ and $Z^5$ are as defined in claim 1.

* * * * *

UNITED STATES PATENT AND TRADEMARK OFFICE
CERTIFICATE OF CORRECTION

PATENT NO. : 6,534,486 B1
DATED : March 18, 2003
INVENTOR(S) : David George Allen et al.

It is certified that error appears in the above-identified patent and that said Letters Patent is hereby corrected as shown below:

Column 24,
Line 35, "sents aryl$_2$CHCH$_2$." should read -- sents aryl$_2$CHCH$_2$-, --

Signed and Sealed this

Twenty-third Day of December, 2003

JAMES E. ROGAN
*Director of the United States Patent and Trademark Office*